(12) United States Patent
Cheng et al.

(10) Patent No.: US 8,988,518 B2
(45) Date of Patent: Mar. 24, 2015

(54) MEDICAL IMAGING SYSTEM

(75) Inventors: Chu-Ming Cheng, Hsinchu (TW); Long-Sheng Liao, Hsinchu (TW); Yi-Wen Chen, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 532 days.

(21) Appl. No.: 13/073,163

(22) Filed: Mar. 28, 2011

(65) Prior Publication Data
US 2012/0249765 A1    Oct. 4, 2012

(51) Int. Cl.
| | |
|---|---|
| *A61B 1/04* | (2006.01) |
| *A61B 1/06* | (2006.01) |
| *A61B 1/00* | (2006.01) |
| *H04N 5/235* | (2006.01) |
| *H04N 5/225* | (2006.01) |
| *A61B 3/12* | (2006.01) |
| *G02B 13/00* | (2006.01) |
| *G02B 23/24* | (2006.01) |

(52) U.S. Cl.
CPC .............. *A61B 1/00188* (2013.01); *A61B 1/04* (2013.01); *A61B 1/042* (2013.01); *H04N 5/2354* (2013.01); *A61B 1/0623* (2013.01); *H04N 5/2256* (2013.01); *A61B 3/12* (2013.01); *G02B 13/005* (2013.01); *G02B 23/2469* (2013.01); *G02B 23/2476* (2013.01); *H04N 2005/2255* (2013.01); *A61B 1/0607* (2013.01)
USPC ................ 348/77; 348/68; 600/109; 600/178

(58) Field of Classification Search
CPC ........ A61B 1/04; A61B 1/042; A61B 1/0623; H04N 5/2256; H04N 5/2354; H04N 2005/2255; G02B 23/2469
See application file for complete search history.

(56) References Cited

U.S. PATENT DOCUMENTS

| | | | |
|---|---|---|---|
| 6,181,474 B1 * | 1/2001 | Ouderkirk et al. ............ 359/629 |
| 2008/0156882 A1 * | 7/2008 | Tsikos et al. .............. 235/462.43 |
| 2009/0270683 A1 * | 10/2009 | Farr et al. ....................... 600/166 |
| 2010/0149519 A1 * | 6/2010 | Toofan ............................. 356/51 |

OTHER PUBLICATIONS

Newport Handbook on Optics, Focusing and Collimating (2006) p. 479.*

* cited by examiner

*Primary Examiner* — Joseph Ustaris
*Assistant Examiner* — Jill Sechser
(74) *Attorney, Agent, or Firm* — Muncy, Geissler, Olds & Lowe, P.C.

(57) ABSTRACT

A medical imaging system includes a first lens set, a light source and an image forming module. The medical imaging system of the present invention configures the light source according to the object-image relationship of lens, so that illuminating light may sufficiently enter a cavity, significantly increasing the luminous efficiency. Also, the image forming and illuminating components are integrated into one system, thereby achieving advantages of reduced volume and cost saving.

9 Claims, 4 Drawing Sheets

MEDICAL IMAGING SYSTEM

BACKGROUND OF THE INVENTION

1. Field of the Invention

The present invention relates to an image capturing system, and more particularly to a medical imaging system achieving a smaller volume and higher luminous efficiency.

2. Description of the Prior Art

Image capturing technology, particularly that for a biological cavity, is required to have an adequate external illumination that can pass through the opening of the cavity to provide illuminating light with sufficient luminance, for there is no light source illuminating the interior of the biological cavity and the opening of the biological cavity is often relatively small, so that the imaging system may capture reflected image forming light to render a clear and accurate image within the cavity for observation or filming.

A prior art illuminating system employed a ring-shaped hollow reflective mirror to reflect light rays of a light source in coordination with a lens set to direct illuminating light into an opening of a cavity. The image light passed through the hollow region of the ring-shaped hollow reflective mirror to form an image. However, normally the luminous intensity distribution of a light source is a Lambertian distribution or Gaussian distribution that has higher intensities in the central region. The ring-shaped hallow reflective mirror was unable to utilize this central portion of the light to provide illumination, thereby causing a low luminous efficiency.

Another prior art illuminating system used a point light source with a reflective mirror and lens set to focus illuminating light at an opening of a cavity, and then captured image forming light from the cavity with an image forming system off axially disposed with respect to the illuminating system to form an image. Although the problem of low luminous efficiency was solved, the off-axis configuration of the illuminating system and the imaging system required more optical components, and raised the manufacturing cost. Besides, the volume and length of the system were also increased, which limited the field of view of the system, and hindered the design of a large field of view and large aperture system. As a result, the illuminating view and the imaging view were different, lowering the capturing accuracy.

In summary, it is highly desirable to provide a system with a reduced volume and higher luminous efficiency.

SUMMARY OF THE INVENTION

The present invention is directed to a medical imaging system which configures a light source according to the object-image relationship of lens, thereby allowing illuminating light to enter an interior of a cavity sufficiently, and integrates an imaging component and illuminating component into one system, thereby achieving advantages of smaller volume and lower cost.

According to an embodiment, the medical imaging system for capturing an image of a cavity with an opening comprises a first lens set, a light source and an image forming module. The first lens set defines a focal point, a first optical axis position and a second optical axis position, wherein the first optical axis position and the second optical axis position are respectively located on the opposite sides of the first lens set on an optical axis and satisfy the following relationship:

$$\frac{1}{D1} + \frac{1}{D2} = \frac{1}{f}$$

wherein D1 is a distance from the first optical axis position to the first lens set, D2 is a distance from the second optical axis position to the first lens set, f is a focal length of the first lens set, and the distance from the first optical axis position to the first lens set is larger than twice the focal length of the first lens set. The light source is disposed off the optical axis of the first lens set, has a distance with the first lens set larger than the focal length and smaller than the distance between the first optical axis position and the first lens set, and is coupled optically with the first lens set to provide illuminating light, wherein the illuminating light directly irradiates on the first lens set, passes through the first lens set, converges in the cavity and then diverges to illuminate the interior of the cavity. The image forming module is disposed on the optical axis for receiving an image forming light reflected by the interior of the cavity through the first lens set to form the image.

The objective, technologies, features and advantages of the present invention will become more apparent from the following description in conjunction with the accompanying drawings, wherein certain embodiments of the present invention are set forth by way of illustration and examples.

DESCRIPTION OF THE PREFERRED EMBODIMENT

Figure 1:
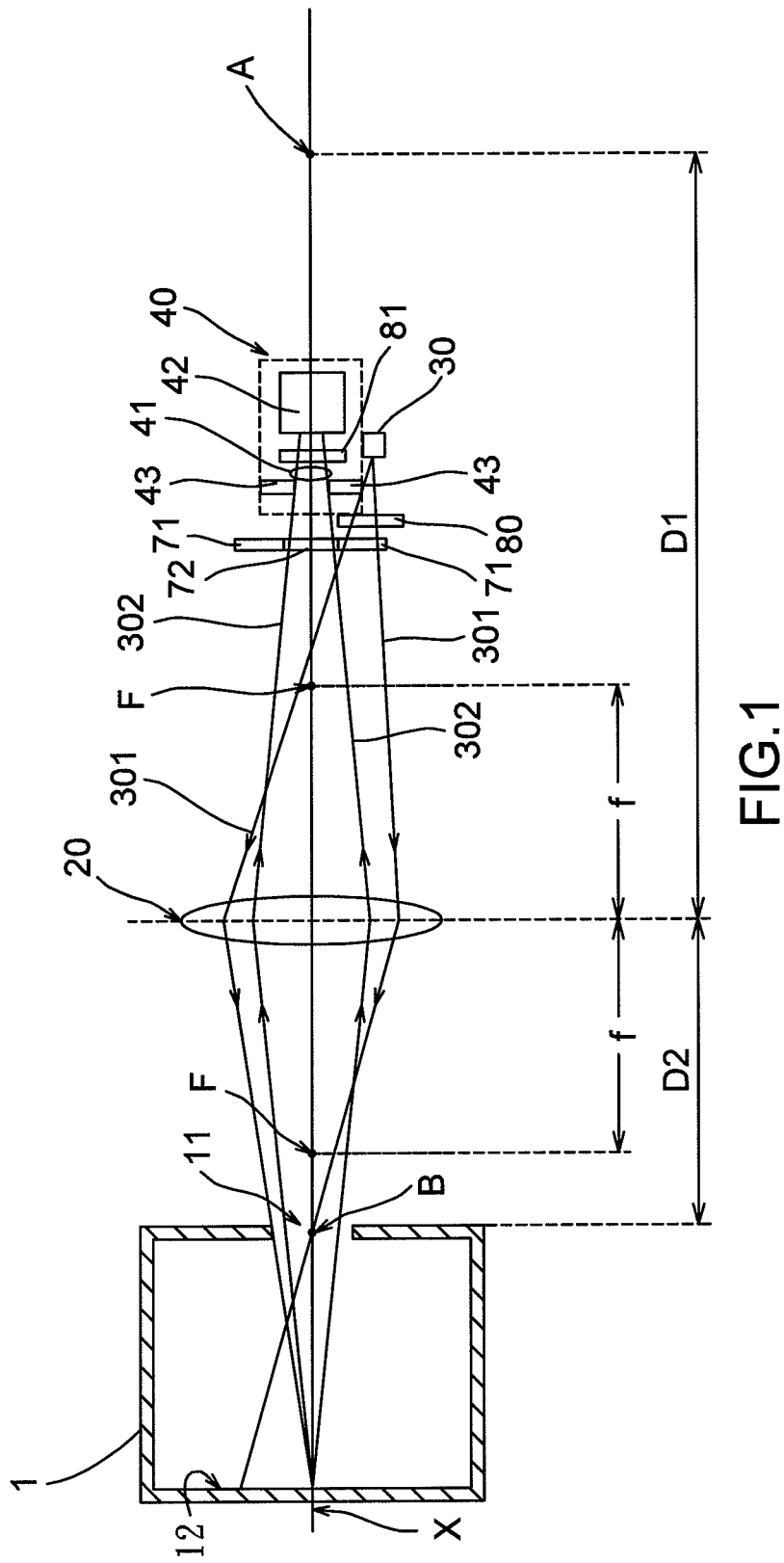
FIG. 1 is a schematic diagram illustrating the medical imaging system according to an embodiment of the present invention.
Figure 2:
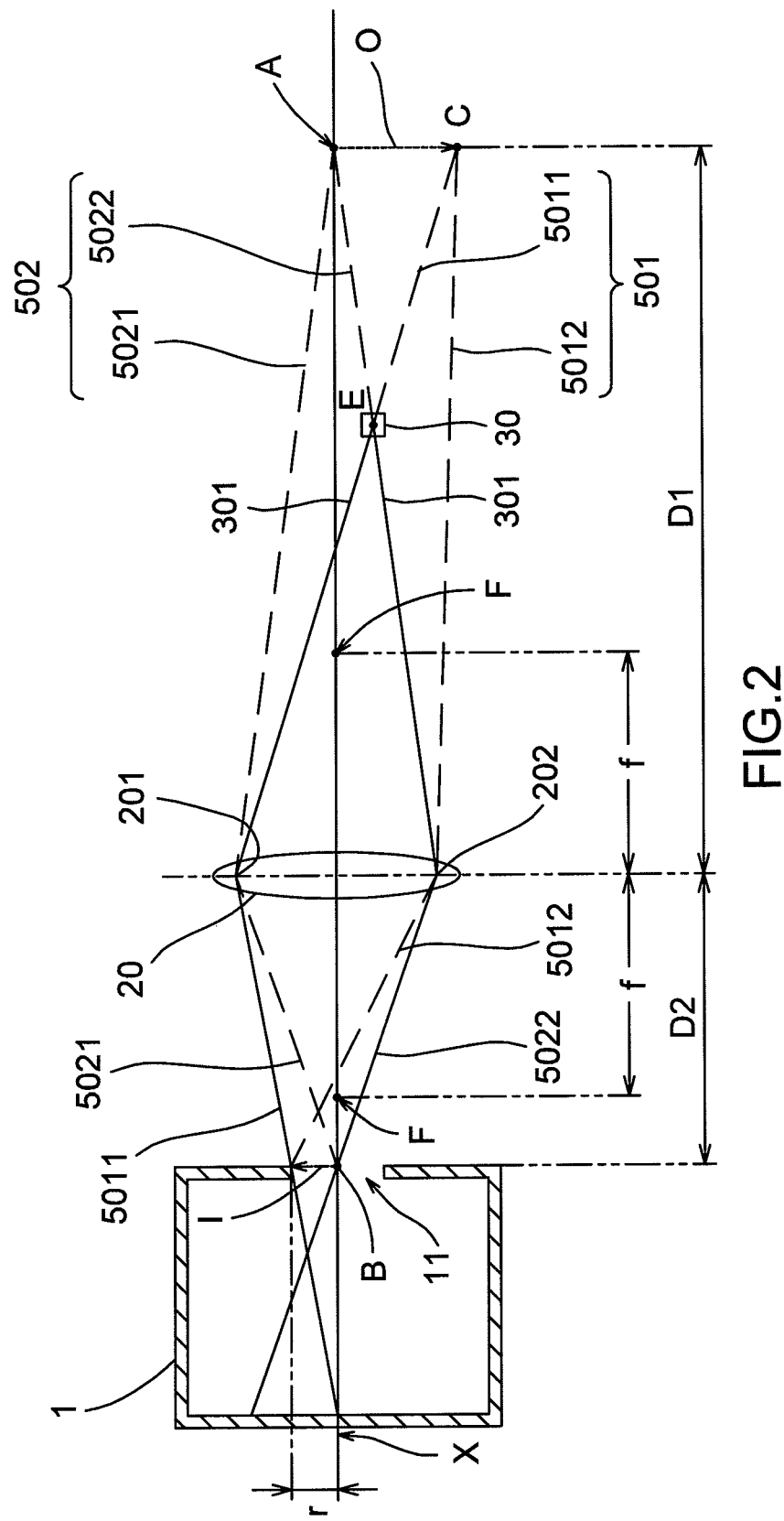
FIG. 2 is a schematic diagram illustrating the method for determining the position of the light source of the medical imaging system according to an embodiment of the present invention.

Referring to FIG. 1 and FIG. 2 simultaneously, FIG. 1 is a schematic diagram of the medical imaging system according to an embodiment; FIG. 2 is a schematic diagram illustrating the method for determining the position of a light source of the medical imaging system according to an embodiment. The medical imaging system of the present invention is for capturing an image in a cavity 1 with an opening 11. In the description below, the directions up, down, right and left accord with the relative positions shown in figures for the convenience of illustration, and should not be considered as limitations of the present invention. The medical imaging system according to an embodiment includes: a first lens set 20, a light source 30 and an image forming module 40. The first lens set 20 has a focal point F with a focal length f. A optical axis X passes through the first lens set 20 and has a first optical axis position A and a second optical axis position B defined thereon, wherein the first optical axis position A and the second optical axis position B are respectively on the opposite sides of the first lens set 20 and satisfy the following relationship:

$$\frac{1}{D1} + \frac{1}{D2} = \frac{1}{f} \qquad \text{eq. 1}$$

$$D1 > f, D2 > f \qquad \text{eq. 2}$$

It can be understood that eq. 1 is the image formation formula of a lens, wherein D1 is the distance from the first optical axis position A to the first lens set 20 and D2 is the distance from the second optical axis position B to the first lens set 20. The light source 30 includes at least a point light source, which may be a light-emitting diode or a light-emitting fiber optics. The light source 30 is disposed off the optical axis X and its distance to the first lens set 20 is greater than the focal length f and smaller than the distance from the first optical axis position A to the first lens set 20. Preferably, the distance D1 from the first optical axis position A to the first lens set 20 is greater than twice the focal length f. The cavity 1 is disposed on the left side of the first lens set, and the distance from the opening 11 of the cavity 1 to the first lens set 20 is substantially equal to the distance D2 from the second optical axis position B to the first lens set 20.

Continuing the above description, the light source 30 is optically coupled with the first lens set 20 and provides illuminating light 301, wherein the illuminating light 301 passes through the first lens set 20, converges inside the cavity 1 and then diverges, thereby illuminating a surface 12 of the interior of the cavity 1. The image forming module 40 is disposed on the optical axis X. According to an embodiment, the image forming module 40 includes a second lens set 41 and an image sensing element 42, and is for accepting image forming light 302 reflected by the surface 12 of the cavity 1. The image forming light 302 passes through the opening 11 of the cavity 1, the first lens set 20 and the second lens set 41 in sequence and reaches the image sensing element 42 to form an image. The image sensing element 42 may be a CCD (charged coupled device), CMOS (complementary metal oxide semiconductor) sensor, film or the combination thereof. According to an embodiment, the image forming module 40 further includes an diaphragm 43 disposed between the first lens set 20 and the light source 30 for limiting light outside the optical axis X from entering the image forming module 40. It can be understood that the first lens set 20 and/or the second lens set 41 may be variable focal length lens sets so that the focal length may be adjusted to form a clear image.

Figure 3:
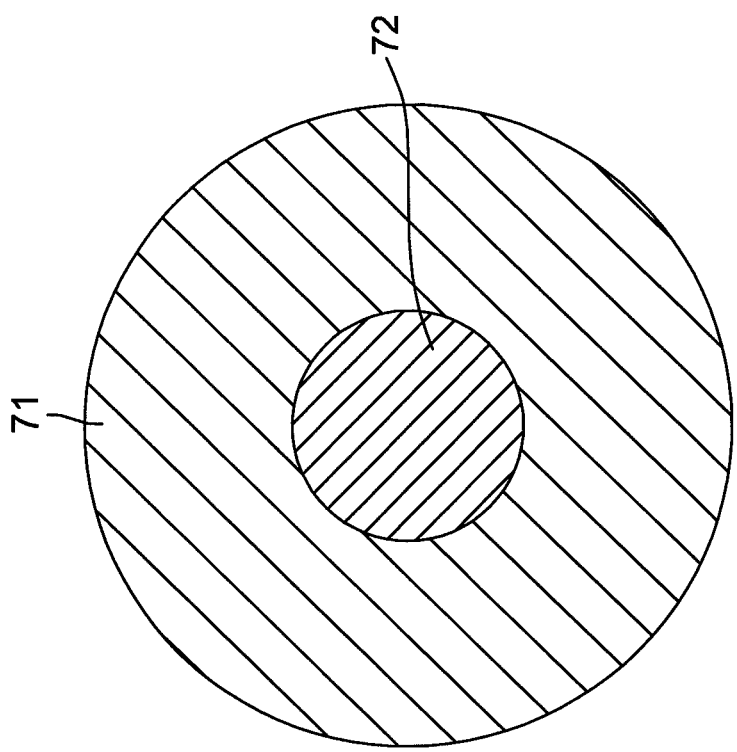
FIG. 3 is a schematic diagram illustrating the first optical polarizing sheet and the second optical polarizing sheet of the medical imaging system according to an embodiment of the present invention.

Referring FIG. 1 and FIG. 3 simultaneously, FIG. 3 is a schematic diagram of a first optical polarizing sheet and a second optical polarizing sheet of the medical imaging system according to an embodiment. As illustrated in FIG. 1, according to an embodiment, the first medical imaging system further includes a first optical polarizing sheet 71 and a second optical polarizing sheet 72, wherein the first optical polarizing sheet 71 is disposed between the light source 30 and the first lens set 20, and is optically coupled with the illuminating light 301 to polarize the illuminating light 301; the second optical polarizing sheet 72 is disposed between the image forming module 40 and the first lens set 20 and is optically coupled with the image forming light 302 to polarize the image forming light 302. The polarization directions of the first optical polarizing sheet 71 and the second optical polarizing sheet 72 are different. For example, the first optical polarizing sheet 71 is a horizontal polarizing sheet and the second optical polarizing sheet 72 is vertical polarizing sheet. The light source 30 emits light passes through the first optical polarizing sheet 71 and then reflected and directed by the first lens set 20 towards the image forming module 40. Because the polarization directions of the light emitted and the second optical polarizing sheet 72 are orthogonal to each other, the light emitted is not able to pass through the second optical polarizing sheet 72 and only the image forming light 302 with the same polarization direction as the second optical polarizing sheet 72 is allowed to pass, thereby enhancing image quality. As illustrated in FIG. 3, according to an embodiment, the first optical polarizing sheet 71 may be annularly disposed around the second optical polarizing sheet 72, but the present invention is not limited to be implemented as such. It can be understood that the first optical polarizing sheet 71 may be integrated with the light source 30 as a single module for emitting the illuminating light 301 with a specific polarized direction.

According to an embodiment, the medical imaging system further includes a light filtering sheet optically coupled with the light source for emitting the illuminating light 301 with a specific range of wavelengths. Alternatively, in another embodiment, the light filtering sheet may be optically coupled with the image forming module 40, so that the image forming module 40 only receives image forming light 302 with a specific range of wavelengths. Preferably, as illustrated in FIG. 1, the medical imaging system according to an embodiment further includes two light filtering sheets 80, 81 disposed respectively for coupling optically with the illuminating light 301 and the image forming light 302. For example, in the embodiment illustrated in FIG. 1, the light filtering sheet 80 is disposed between the light source 30 and the first optical polarizing sheet 71; the light filtering sheet 81 is disposed between the second lens set 41 of the image forming module 40 and the image sensing element 42, but the present invention is not limited to be implemented as such. The light filtering sheets 80, 81 are for filtering out a wavelength range of light. Based on the characteristics of the light source 30 and the surface 12 of the cavity 1, only the illuminating light 301 and image forming light 302 with a specific wavelength is allowed to pass through, thereby enhancing the application range and the image quality.

FIG. 2 and the description below illustrate the method for determining the position of the light source in the medical imaging system of the present invention. It is noted that for convenience of illustration, the image forming module 40 is omitted in FIG. 2. Suppose there is an image I with an image height r on the second optical axis position B. Then according to the image formation formula of a lens (eq. 1), there is a virtual object O in the direction of the first optical axis position A. The apex of the object O is defined to be an off-axis position C, and the projected position of the off-axis position C on the optical axis X is the first optical axis position A. The distance between the off-axis position C and the first optical axis position A is the height of the object O and the value of which is equal to the image height r multiplied by the magnification factor of the first lens set 20.

Suppose the object O emits light of a first light cone 501 from the off-axis position C. The first light cone 501 includes upper edge light 5011 of the first light cone 501 and lower edge light 5012 of the first light cone 501, wherein the upper edge light 5011 of the first light cone 501 intersects with the first lens set 20 at the first optical border 201; the lower edge light 5012 intersects with the first lens set 20 at the second optical border 202. The off-axis position C and the first optical border 201 are on the opposite sides of the optical axis X, and the first optical border 201 and the second optical border 202 are on the opposites of the optical axis X. It has to be clarified that the first optical border 201 and the second optical border 202 refer to the borders within which the first lens set 20 may generate optical effects, e.g. the light emitted by the light source 30 may couple optically with the object O on the first optical axis position A and form the image I on the second optical axis position B.

Continuing the above description, the object O emits the light of a second light cone 502 on the first optical axis position A. The second light cone 502 includes upper edge light 5021 of the second light cone 502 and lower edge light 5022 of the second light cone 502, respectively intersect with the first lens set 20 at the first optical border 201 and the second optical border 202. The light source 30 is disposed at the intersecting point E of the connecting line of the off-axis position C and the first optical border 201 of the first lens set 20, and the connecting line of the first optical axis position A and the second optical border 202 of the first lens set 20. Then, the illuminating light 301 emitted by the light source 30 disposed at the intersecting point E would cover the range between the first optical border 201 and the second optical border 202 of the first lens set 20, i.e., the illuminating light 301 travels along the upper edge light 5011 of the first light cone 501 and the lower edge light 5022 of the second light cone 502 to couple optically with the first lens set 20, and converges between the focal point F of the first lens set 20 and the surface 12 of the interior of the cavity 1, rather than converges at the second optical axis position B or the focal point F of the first lens set 20. Therefore, the height of the image I is smaller than half of the inner radius of the opening 11 whereby the illuminating light 301 may sufficiently enter the interior of the cavity 1, significantly increasing the luminous efficiency.

Besides, as shown in FIG. 2, the deflection angle of the illuminating light 301 along the path of the upper edge light 5011 of the first light cone 501 after coupling optically with the first lens set 20 is smaller than the deflection angle of the illuminating light 301 along the path of the lower edge light 5022 of the second light cone 502 after coupling optically with the first lens set 20. Hence, the illuminating light 301 within the space between the second optical axis position B and position where the illuminating light 301 converges in the cavity 1 has a smaller height variation, thereby allowing the illuminating light 301 to have a larger tolerance moving forward or backward. That is, as long as the opening 11 of the cavity 1 is disposed within this range, the illuminating light 301 may sufficiently enter the interior of the cavity 1. It can be understood that the medical imaging system of the present invention may adjust the position where the light source 30 is disposed (the intersecting point E) along the direction perpendicular to the optical axis X according to the size of the opening 11 of the cavity 1. When the intersecting point E is located further from the optical axis X, a wide field and large aperture image forming module 40 may be used. Since the medical imaging system of the present invention integrates the image formation and illuminating elements within a system, it has the advantages of smaller volume and lower cost. In addition, the cavity 1 may be an eye, and the opening 11 may be a pupil. The cavity 1 may also be organs such as an ear, nose, throat, skin, abdomen and stomach. The medical imaging system of the present invention may be widely applied in the fields of endoscopy (optical tube type or capsule type) and biological microscopy or any class of digital medical imaging system.

Figure 4B:
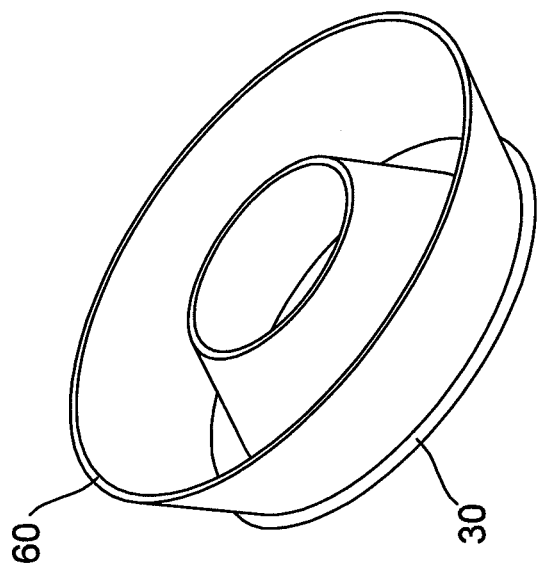
FIG. 4B is a schematic diagram illustrating the light source of the medical imaging system according to an embodiment of the present invention.
Figure 4A:
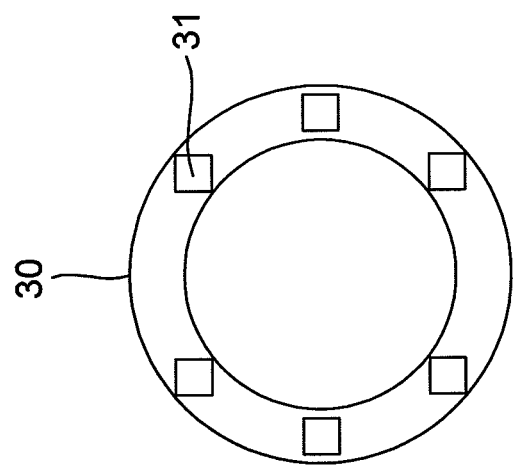
FIG. 4A is a schematic diagram illustrating the light source of the medical imaging system according to an embodiment of the present invention.

Moreover, the illuminating light 301 of the light source 30 is directly optically coupled with the first lens set 20, so the distribution of luminance would not be non-uniform when the light source 30 is disposed off the optical axis X, thereby increasing the luminous efficiency. Also, because the light source 30 is disposed off the optical axis X, there will be no phantom image problem generated during image formation. According to an embodiment, the opening 11 of the cavity 1 is symmetrical with respect to the optical axis X, and the inner radius of the opening 11 is twice the image height r, and the illuminating light 301 pass through the range of half the cross section of the opening 11. Preferably, the illuminating light 30 is an annular light source such as one shown in FIG. 4A, a schematic diagram illustrating the light source of the medical imaging system according to an embodiment. The light source 30 may be a plurality of light-emitting diodes 31 arranged annularly around and symmetrically with respect to the optical axis X, thereby the illuminating light 301 may sufficiently cover the opening 11, and providing uniform illumination. The illuminating light 301 converges inside the cavity 1 into an annular light spot and then diverges to illuminate the interior of the cavity 1. It can be understood that the aforementioned annular light source may also be formed by a plurality of light-emitting fiber optics arranged annularly. In another embodiment, the light source 30 further includes an annular light guide element (not illustrated), forming an annular light source. According to another embodiment, the medical imaging system further includes a reflecting device 60. As illustrated in FIG. 4B, the light source 30 is an annular light source, and the reflecting device 60 may be a hallow reflector cover coupled optically with the light source 30 for reflecting the light emitted by the light source 30 to the first lens set 20 to increase the luminous efficiency.

In summary, in the medical imaging system of the present invention, the off-axis position of the light source is determined according to the intersecting point of the edges of the first light cone and the second light cone that form an image on the second optical axis position after an object on the first optical axis position is optically coupled with the first lens set. The light source is off axially disposed and the illuminating light emitted is directly optically coupled with the first lens set, and therefore does not results in phantom images or non-uniform luminance distribution. The illuminating light passes through the first lens set and converges inside the cavity, providing sufficient illumination at the opening of the cavity, and greatly enhancing the luminous efficiency. In addition, disposing the light source on an off-axis position allows a greater tolerance for moving the light source back and forth, and integrating the imaging and illuminating components within one system may provide the advantages of reduced volume and lower cost.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

The invention claimed is:

1. A medical imaging system for capturing an image of a cavity with an opening comprising:
a first lens set defining a focal point, a first optical axis position and a second optical axis position, wherein the first optical axis position and the second optical axis position are respectively located on the opposite sides of the first lens set on an optical axis and satisfy the following relationship:

$$\frac{1}{D1} + \frac{1}{D2} = \frac{1}{f}$$

wherein D1 is a distance from the first optical axis position to the first lens set, D2 is a distance from the second optical axis position to the first lens set, f is a focal length of the first lens set, and the distance from the first optical axis position to the first lens set is larger than twice the focal length of the first lens set;

a light source disposed off the optical axis of the first lens set, having a distance with the first lens set larger than the focal length and smaller than the distance between the first optical axis position and the first lens set, and coupled optically with the first lens set to provide illuminating light, wherein the illuminating light directly irradiates on the first lens set, passes through the first lens set, converges in the cavity and then diverges to illuminate the interior of the cavity; and an image forming module disposed on the optical axis for receiving an image forming light reflected by the interior of the cavity through the first lens set to form the image.

2. The medical imaging system according to claim 1, wherein the light source is disposed at an intersecting point of the connecting line of an off-axis position and a first optical border of the first lens set, and the connecting line of the first optical axis position and a second optical border of the first lens set, wherein the off-axis position and the first optical border are respectively on the opposite sides of the optical axis; the off-axis position is off from the optical axis, and the first optical axis position is the projected position of the off-axis position onto the optical axis.

3. The medical imaging system according to claim 1, wherein the image forming module comprises a second lens set and an image sensing element, and the image forming light passes through the opening of the cavity, the first lens set and the second lens set to reach the image sensing element, wherein the image sensing element comprises a CCD, CMOS sensor, film or the combination thereof.

4. The medical imaging system according to claim 3, wherein the second lens set is a variable focal length lens set, wherein the image forming module further comprises a diaphragm for limiting light outside the optical axis from entering the image forming module.

5. The medical imaging system according to claim 1, further comprises:
 a first optical polarizing sheet disposed between the light source and the first lens set for polarizing the illuminating light; and
 a second optical polarizing sheet disposed between the image forming module and the first lens set for polarizing the image forming light, wherein the first optical polarizing sheet and the second optical polarizing sheet have different polarization directions.

6. The medical imaging system according to claim 1, further comprises at least a light filtering sheet disposed for coupling with at least one of the illuminating light and image forming light to filter out a wavelength range of light.

7. The medical imaging system according to claim 1, wherein the light source comprises at least a point light source or an annular light source.

8. The medical imaging system according to claim 1, wherein the light source comprises a light-emitting diode, a plurality of annularly arranged light-emitting diodes or a fiber optics.

9. The medical imaging system according to claim 1, further comprises a reflecting device optically coupled with the light source for reflecting the light emitted by the light source to the first lens set.

* * * * *